United States Patent [19]
Wang et al.

[11] Patent Number: 6,075,150
[45] Date of Patent: Jun. 13, 2000

[54] α-KETOAMIDE INHIBITORS OF 20S PROTEASOME

[75] Inventors: Lisa Wang, Burlingame; Robert T. Lum, Palo Alto; Steven R. Schow, Redwood City; Alison Joly, San Mateo, all of Calif.; Suresh Kerwar, Westchester, N.Y.; Michael M Wick, Chestnut Hill, Mass.

[73] Assignee: CV Therapeutics, Inc., Palo Alto, Calif.

[21] Appl. No.: 09/013,365

[22] Filed: Jan. 26, 1998

[51] Int. Cl.$^7$ ......................... C07D 209/12; A01N 43/38
[52] U.S. Cl. .............................. 548/494; 514/419
[58] Field of Search ................... 548/486, 494; 562/448; 514/419

[56] References Cited

U.S. PATENT DOCUMENTS 5,656,604  8/1997  Hemmi et al. .

FOREIGN PATENT DOCUMENTS

| | | |
|---|---|---|
| 0 468 339 | 1/1992 | European Pat. Off. . |
| WO 88/09789 | 12/1988 | WIPO . |
| WO 95/24914 | 9/1995 | WIPO . |
| WO 95/25533 | 9/1995 | WIPO . |
| WO 96/13266 | 5/1996 | WIPO . |
| WO 98/13061 | 4/1998 | WIPO . |

OTHER PUBLICATIONS

Database CAPLUS on STN, Acc. No. 1981:137817, Johansen et al., 'Enzymic production of peptides' EP 17485 abstract, 1981.

Coux et al., *Annu. Rev. Biochem.*, vol. 65, pp. 801–847, Structure and Functions of the 20S and 26S Proteasomes (1996).

Löwe et al., *Science*, vol. 268, pp. 533–539, Research Article, Crystal Structure of the 20S Proteasome from the Archaeon *T. acidophilum* at 3.4 Å Resolution (1995).

Groll, M., et al., *Nature*, vol. 386, pp. 463–471, Structure of 20S Proteasome from Yeast at 2.4 A Resolution (1997).

Dahlmann et al., *FEBS Letters*, vol. 251, No. 1,2, pp. 125–131, the Multicatalytic Proteinase (prosome) is Ubiquitous From Eukaryotes to Archaebacteria (1989).

Seemüller et al., *FEBS Letters*, vol. 359, pp. 173–178, The Proteasome From *Thermoplasma Acidophilum* is Neither a Cysteine Nor a Serine Protease (1995).

Orlowski, *Biochemistry*, vol. 29, No. 45, pp. 10289–10297, The Multicatalytic Proteinase Complex, a Major Extralysosomal Proteolytic System (1990).

Vinitsky et al., *Biochemistry*, vol. 31, pp. 9421–9428, Inhibition of the Chymotrypsin–like Activity of the Pituitary Multicatalytic Proteinase Complex (1992).

Tsubuki et al., *Biochemical and Biophysical Research Communications*, vol. 196, No. 3, pp. 1195–1201, Purification and Characterization of a Z–Leu—Leu—Leu–MCA Degrading Protease Expected to Regulate Neurite Formation: A Novel Catalytic Activity in Proteasome (1993).

Rock et al., *Cell*, vol. 78, pp. 761–771, Inhibitors of the Proteasome Block the Degradation of Most Cell Proteins and the Generation of Peptides Presented on MHC Class I Molecules (1994).

Iqbal et al., *J. Med. Chem.*, vol. 38, pp. 2276–2277, Potent Inhibitors of Proteasome (1995).

Iqbal et al., *Bioorganic & Medicinal Chemistry Letters*, vol. 6, No. 3, pp. 287–290, Potent α–Ketocarbonyl and Boronic Ester Derived Inhibitors of Proteasome (1996).

Spaltenstein, et al., *Tet. Letters*, vol. 37, pp. 1343–1346, Design and Synthesis of Novel Protease Inhibitors (1996).

Fenteany et al., *Science*, vol. 268, pp. 726–731, Inhibition of Proteasome Activities and Subunit–Specific Amino–terminal Threonine Modification by Lactacystin (1995).

(List continued on next page.)

*Primary Examiner*—Gary Geist
*Assistant Examiner*—Brian J. Davis
*Attorney, Agent, or Firm*—McDonnell Boehnen Hulbert & Berghoff

[57] ABSTRACT

α-ketoamide compounds useful for treating disorders mediated by 20S proteasome in mammals having the following formula:

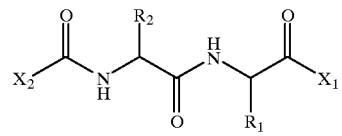

wherein $X_2$ is Ar or Ar—$X_3$ wherein $X_3$ is —C=O, or —$CH_2CO$—, and wherein Ar is phenyl, substituted phenyl, indole, substituted indoles, and any other heteroaryls; $R_1$, and $R_2$ are each individually selected from the side chains of the known natural α-amino acids and unnatural amino acids, hydrogen, 1–10 carbon linear and branched alkyl, 1–10 carbon linear and branched substituted alkyl, aryl, substituted aryl, 1–10 carbon linear, branched substituted aryl, alkoxyaryl, 3–8 carbon cycloalkyl, heterocycle substituted heterocycle, heteroaryl and substituted heteroaryl; $X_1$ is selected from hydroxide, monoalkylamino, dialkylamino, alkoxide, arylkoxide and

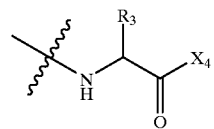

wherein $X_4$ is hydroxide, arylamino, monoalkylamino, dialkylamino, alkoxide, or arylalkoxide; and $R_3$ is selected from the known natural α-amino acids, unnatural amino acids, hydrogen, 1–10 carbon linear and branched alkyl, 1–10 carbon linear and branched substituted alkyl, aryl, substituted aryl, 1–10 carbon linear and branched substituted aryl, alkoxyaryl, 3–8 carbon cycloalkyl, heterocycle, substituted heterocycle, heteroaryl and substituted heteroaryl.

2 Claims, No Drawings

OTHER PUBLICATIONS

Omura et al., *The Journal of Antibiotics*, vol. 44, No. 1, pp. 117–118, Structure of Lactacystin, A New Microbial Metabolite Which Induces Differentiation of Neuroblastoma Cells (1990).

Fenteany et al., *Proc. Natl. Acad. Sci, USA*, vol. 91, pp. 3358–3362, A β–Lactone Related to Lactacystin Induces Neurite Outgrowth in a Neuroblastoma Cell Line and Inhibits Cell Cycle Progression in an Osteosarcoma Cell Line (1994).

Ciechanover, *Cell*, vol. 79, pp. 13–21, the Ubiquitin–Proteasome Proteolytic Pathway (1994).

Palombella et al., *Cell*, vol. 78, pp. 773–785, The Ubiquitin–Proteasome Pathway is Required for Processing the NF–κB1 Precursor Protein and the Activation of NF–κB (1994).

Glotzer et al., *Nature*, vol. 349, pp. 132–138, Cyclin is Degraded by the Ubiquitin Pathway (1991).

DeSettimo et al. "Synthesis and benzodiazepine receptor affinity of N–(indol–3–ylgoxylyl)–dipeptide derivatives. Structural requirements for inverse agonist/antagonist receptor interations", *Drug Des. Discovery*, 10: 199–211 (1993).

Chemical Abstracts, vol. 89, No. 15, Oct. 9, 1978.

Lum et al. "Selective inhibition of the chymotrypsin–like activity of the 20S proteasome by 5–methoxy–1–indanone dipeptide benzamides" *Bioorganic & Medicinal Chemistry Letters*, 8:209–214 (1998).

α-KETOAMIDE INHIBITORS OF 20S PROTEASOME

BACKGROUND OF THE INVENTION

The multicatalytic proteinase or the proteasome is a highly conserved cellular structure that is responsible for the ATP-dependent proteolysis of most cellular proteins (Coux, O., Tanaka, K. and Goldberg, A. 1996 Ann. Rev. Biochem. 65, 801–847). The 20S proteasome contains the catalytic core of the complex and has been crystallized from the archaebacteria Thermoplasma acidophilum (Lowe, J., Stock, D., Jap, B., Zwicki, P., Bauminster, W. and Huber, R. 1995 Science 268, 533–539) and from the yeast Saccharomyces cerevisiae (Groll, M., Ditzel, L., Lowe, J., Stock, D., Bochtler, M., Bartunik, HD and Huber, R. 1997 Nature 386, 463–471). Unlike the archaebacterial proteasome that primarily exhibits chymotrypsin-like proteolytic activity (Dahlmann, B., Kopp, F., Kuehn, L., Niedel, B., Pfeifer, G. 1989 FEBSLett. 251, 125–131; Seemuller, E., Lupas, A., Zuw, F., Zwickl, P and Baumeister, W. FEBS Lett. 359, 173, (1995) the eukaryotic proteasome contains at least five identifiable proteolytic activities. Three of these activities are similar in specificity to chymotrypsin, trypsin and peptidylglutamyl peptidase. The two other activities described exhibit a preference for cleavage of peptide bonds on the carboxyl side of branched chain amino acids (BrAAP) and toward peptide bonds between short chain neutral amino acids (SnAAP) (Orlowski, M. 1990 Biochemistry 29, 10289–10297).

Although the 20S proteasome contains the proteolytic core, it cannot degrade proteins in vivo unless it is complexed with a 19S cap, at either end of its structure, which itself contains multiple ATPase activities. This larger structure is known as the 26S proteasome and will rapidly degrade proteins that have been targeted for degradation by the addition of multiple molecules of the 8.5-kDa polypeptide, ubiquitin (reviewed in Coux, O., Tanaka, K. and Goldberg, A. 1996 Ann.Rev. Biochem. 65, 801–847).

A large number of substrate-derived functionalities have been used as potential serine- and thiol protease inhibitors. Several of these motifs have been described as inhibitors to the proteasome. These include the peptide aldehydes (Vinitsky, A., Michaud, C,, Powers, J. and Orlowski, M. 1992 Biochemistry 31, 9421–9428; Tsubuki, S., Hiroshi, K., Saito, Y., Miyashita, N., Inomata, M., and Kawashima, S. 1993 Biochem.Biophys.Res.Commun. 196,1195–1201; Rock, K, I., Gramm, C., Rothstein, L., Clark, K., Stein, R., Dick, L., Hwang, D. and Goldberg, A. L. (1994) Cell 78, 761–771) N-acetyl-L-leucinyl-L-leucinyl-L-norleucinal (ALLN) and N-acetyl-L-leucinyl-1-leucinyl-methional (LLM) with the most potent inhibitor of this type being N-carbobenzoxyl-1-L-leucinyl-L-leucinyl-L-norvalinal (MG 115). Other reports have described a series of dipeptide inhibitors that have $IC_{50}$ values in the 10 to 100 nM range (Iqbal, M., Chatterjee S., Kauer, J. C., Das, M., Messina, P., Freed, B., Biazzo, W and Siman, R. 1995 I-Med.Chem. 38, 2276–2277). A series of α-ketocarbonyl and boronic ester derived dipeptides (Iqbai, M., Chatterjee, S., Kauer, J. C., Mallamo, J. P., Messina, P. A., Reiboldt, A. and Siman, R. 1996 Bioorg. Med-Chem. Lett 6, 287–290) and epoxyketones (Spattenstein, A., Leban, JJ., Huang, J. J., Reinhardt, K. R., Viveros, O. H., Sigafoos, J. and Crouch, R. 1996 Tet. Lett. 37, 1434–1346) have also been described that are potent inhibitors of the proteasome.

A different compound that exhibits specificity in inhibiting proteasome activity is Lactacystin (Fenteany, G., Standaert, R. F., Lane, W. S., Choi, S., Corey, E. J. and Schreiber, S. L. 1995 Science 268, 726–731) which is a Streptomyces metabolite. This molecule was originally discovered for its ability to induce neurite outgrowth in a neuroblastoma cell line (Omura, S., Matsuzaki, K., Fujimoto, T., Kosuge, K., Furuya, T., Fujita, S. and Nakagawa, A. 1991 J.Antibiot. 44, 117–118) and later was shown to inhibit the proliferation of several cell types (Fenteany, G., Standaert, R. F., Reichard, G. A., Corey, E. J. and Schreiber, S. L. 1994 Proc.Nat'l. Acad.Sci. USA 91, 3358–3362).

It is now well established that the proteasome is a major extralysosomal proteolytic system involved in the proteolytic pathways essential for diverse cellular functions such as cell division, antigen processing and the degradation of short-lived regulatory proteins such as oncogene products, cyclins and transcription factors (Ciechanover, A. (1994) Cell 79, 13–21; Palombell, V. J., Rando, O. J., Goldberg, A. L. and Maniatis, T. 1994 Cell 78, 773–785). For example, the active form of NF-κB is a heterodimer consisting of a p65 and a p50 subunit. The latter is present in the cytosol as an inactive precursor (p105). The proteolytic processing of p105 to generate p50 occurs via the ubiquitin-proteasome pathway. Additionally, processed p50 and p65 are maintained in the cytosol as an inactive complex bound to the inhibitory protein IκB. Inflammatory stimuli such as LPS activate NF-κB by initiating the signalling pathway which leads to the degradation of IκB. These signals also stimulate the processing of p105 into p50. Thus two proteolytic events, both governed by the ubiquitin-proteasome pathway, are required for signal induced activation of NF-κB.

The observation that ubiquitin-mediated proteasomal proteolysis plays a critical role in the activation of NF-κB could be exploited clinically by the use of inhibitors directed toward the proteasome. Abnormal activation of NF-κB followed by the stimulation of cytokine synthesis has been observed in a variety of inflammatory and infectious diseases. Activation of NF-κB is also essential for angiogenesis and for expression of adhesion molecules (CAMs and selects), thus proteasome inhibitors may also have utility in the treatment of diseases associated with the vascular system.

It is well documented that the ubiquitin-proteasome pathway is critical for the regulated destruction of cyclins that govern the exit from mitosis and allow cells to progress into the next phase of the cell cycle (Glotzer, M., Murray, A. W. and Kirschner, M. W. (1991) Nature 349, 132–138). Thus, inhibiting the degradation of cyclins by using proteasome inhibitors causes growth arrest. Therefore another potential utility of proteasome inhibitors is their use in the treatment of diseases that result from abberrant cell division.

Several classes of peptidic inhibitors of 20S proteasome have been reported in the recent literature. The α-ketoamide group has been used in protease inhibitors for numerous indications. Specifically, a series of α-ketocarbonyl and boronic ester derived dipeptides (Iqbal, M., Chatterjee, S., Kauer, J. C., Mallamo, J. P., Messina, P. A., Reiboldt, A. and Siman, R. 1996 Bioorg. Med. Chem. Lett 6, 287–290) have been reported as potent inhibitors of 20S proteasomal function. Derivatives of 3-indolepyruvic acid have been claimed as pharmaceutically active compounds for the treatment of disturbances of the central nervous system (De Luca, et al WO 88/09789) through a mechanism that modulates kynurenic acid levels in the brain.

Even though various compositions have been discovered that inhibit cell proliferation to some degree, there remains a need for more potent compounds that inhibit cell proliferation via the 20S proteasome.

SUMMARY OF THE INVENTION

It is an object of this invention to provide a method for inhibiting cell proliferation in mammals that uses a therapeutically effective amount of a composition heretofore unknown for its cell proliferative inhibition properties.

It is also an object of this invention to provide a method for the treatment of diseases that may be affected by the inhibition of proteosomal function.

Further, it is an object of this invention to provide a method for the treatment of proliferative diseases that operates by inhibiting proteasomal function.

It is another object of this invention to use a therapeutically effective amount of the compositions described herein to inhibit cell proliferative disorders in humans.

Yet another object of this invention is the use of a therapeutically effective amount of the compositions described herein to inhibit proteasomal function.

In one embodiment, this invention is a composition of matter having the formula:

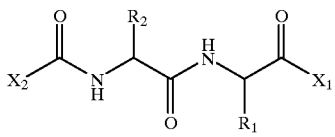

wherein $X_2$ is Ar or Ar—$X_3$ wherein $X_3$ is —C=O, or —CH$_2$CO—, and wherein Ar is phenyl, substituted phenyl, indole, substituted indoles, and any other heteroaryls; $R_1$, and $R_2$ are each individually selected from the side chains of the known natural α-amino acids and unnatural amino acids, hydrogen, 1–10 carbon linear and branched alkyl, 1–10 carbon linear and branched substituted alkyl, aryl, substituted aryl, 1–10 carbon linear, branched substituted aryl, alkoxyaryl, 3–8 carbon cycloalkyl, heterocycle substituted heterocycle, heteroaryl and substituted heteroaryl; $X_1$ is selected from hydroxide, monoalkylamino, dialkylamino, alkoxide, arylkoxide and

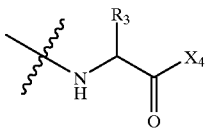

wherein $X_4$ is hydroxide, arylamino, monoalkylamino, dialkylamino, alkoxide, or arylalkoxide; and $R_3$ is selected from the known natural α-amino acids, unnatural amino acids, hydrogen, 1–10 carbon linear and branched alkyl, 1–10 carbon linear and branched substituted alkyl, aryl, substituted aryl, 1–10 carbon linear and branched substituted aryl, alkoxyaryl, 3–8 carbon cycloalkyl, heterocycle, substituted heterocycle, heteroaryl and substituted heteroaryl.

In another embodiment, this invention is a method for inhibiting proteasomal protease factor in mammals comprising administering a therapeutically effective amount of the composition disclosed above to the mammal.

In still another embodiment, this invention is a pharmaceutical composition of matter comprising the composition of claim 1 and one or more pharmaceutical excipients.

DESCRIPTION OF THE CURRENT EMBODIMENT

The invention is a method for inhibiting cell proliferation disorders, infectious diseases, and immunological diseases in mammals, and especially in humans, using compositions having the following general formula:

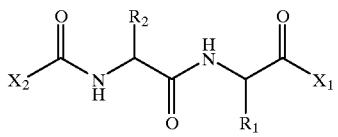

where:
$X_2$ is Ar or Ar—$X_3$ wherein $X_3$ is —C=O, —CH$_2$CO—, or (CH$_2$)n where n=0–2 and wherein Ar is phenyl, substituted phenyl, indole, substituted indoles, and any other heteroaryl.

$R_1$, and $R_2$ are each individually selected from the side chains of the known natural (α-amino acids and unnatural amino acids: hydrogen, 1–10 carbon linear and branched alkyl, 1–10 carbon linear and branched substituted alkyl, aryl and substituted aryl, 1–10 carbon linear and branched substituted aryl, alkoxyaryl, 3–8 carbon cycloalkyl, heterocycle and substituted heterocycle, or heteroaryl and substituted heteroaryl. $R_2$ is preferably biaryl or biphenyl. $R_1$ is preferably isobutyl. $X_1$ is selected from —OH, mono or dialkylamino, alkoxide, arylkoxide and

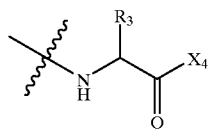

wherein:
$X_4$ is —OH, arylamino, mono or dialkylamino, alkoxide, or arylalkoxide; and preferably —OH $R_3$ is selected from the side chains of known natural α-amino acids and unnatural amino acids, hydrogen, 1–10 carbon linear alkyl and branched alkyl substituents, 1–10 carbon linear and branched substituted alkyl, aryl and substituted aryl, 1–10 carbon linear and branched substituted aryl, alkoxyaryl, 3–8 carbon cycloalkyl, heterocycle and substituted heterocycle, or heteroaryl and substituted heteroaryl. R3 is preferably CO$_2$H, CH$_2$CO$_2$H, (CH$_2$)$_2$CO$_2$H, Arg, Lys, Asn, Gln, Asp, Glu, Phe, and Nle.

The following are definitions for certain terms used herein.

"Halogen" refers to fluorine, bromine, chlorine, and iodine atoms.

"Hydroxyl" refers to the group —OH.

"Thiol" or "mercapto" refers to the group —SH.

"alkyl" refers to a cyclic, branched or straight chain, alkyl group of one to ten carbon atoms. This term is further exemplified by such groups as methyl, ethyl, n-propyl, i-propyl, n-butyl, t-butyl, i-butyl (or 3-methylpropyl), cyclopropylmethyl, i-amyl, n-amyl, n-hexyl and the like.

"Substituted alkyl" refers to lower alkyl as just described including one or more groups such as hydroxyl, thiol, alkylthiol, halogen, alkoxy, amino, amido, carboxyl, cycloalkyl, substituted cycloalkyl, heterocycle, cycloheteroalkyl, substituted cycloheteroalkyl, acyl, carboxyl, aryl, substituted aryl, aryloxy, hetaryl, substituted hetaryl, aralkyl, heteroaralkyl, alkyl alkenyl, alkyl alkynyl, alkyl cycloalkyl, alkyl cycloheteroalkyl, cyano. These groups may be attached to any carbon atom of the lower alkyl moiety.

"Aryloxy" denotes groups —OAr, where Ar is an aryl, substituted aryl, heteroaryl, or substituted heteroaryl group as defined below.

"Amino" denotes the group NRR', where R and R' may independently be hydrogen, lower alkyl, substituted lower alkyl, aryl, substituted aryl, hetaryl, or substituted hetaryl as defined below or acyl.

"Amido" denotes the group —C(O)NRR', where R and R' may independently by hydrogen, lower alkyl, substituted lower alkyl, aryl, substituted aryl, hetaryl, substituted hetaryl as defined below.

"Carboxyl" denotes the group —C(O)OR, where R may independently be hydrogen, lower alkyl, substituted lower alkyl, aryl, substituted aryl, hetaryl, substituted hetaryl and the like as defined.

"Aryl" or "Ar" refers to an aromatic carbocyclic group having at least one aromatic ring (e.g., phenyl or biphenyl) or multiple condensed rings in which at least one ring is aromatic, (e.g., 1,2,3,4-tetrahydronaphthyl, naphthyl, anthryl, or phenanthryl).

"Substituted aryl" refers to aryl optionally substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heterocycle" refers to a saturated, unsaturated, or aromatic carbocyclic group having a single ring (e.g., morpholino, pyridyl or furyl) or multiple condensed rings (e.g., naphthpyridyl, quinoxalyl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Heteroaryl" or "hetar" refers to a heterocycle in which at least one heterocyclic ring is aromatic. Preferred heteroaryls are phenyl, substituted phenyl, indole and substituted indoles.

"Substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido and the like.

"Cycloalkyl" refers to a divalent cyclic or polycyclic alkyl group containing 3 to 15 carbon atoms.

"Substituted cycloalkyl" refers to a cycloalkyl group comprising one or more substituents with, e.g., halogen, lower alkyl, substituted lower alkyl, alkoxy, alkylthio, acetylene, aryl, aryloxy, heterocycle, hetaryl, substituted hetaryl, nitro, cyano, thiol, sulfamido and the like.

Examples of compounds that may be useful in the therapeutic methods of this invention, and specifically, useful as inhibitors of proteosomal function, are identified in Table 1 below:

Examples of compounds that may be useful in the therapeutic method of this invention (specifically, useful as inhibitors of proteosomal function) are listed in the table below:

TABLE I

Compositions used to inhibit 20S proteosome

| # | Ar | $X_3$ | $R_2$ | $R_1$ | $X_1$ | $R_3$ | $X_4$ |
|---|------|--------|---|---|------|--------|------|
| 1 | phenyl | $CH_2CO$ | 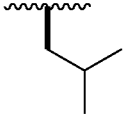 |  | OH | | |
| 2 | Indole | $CH_2CO$ | 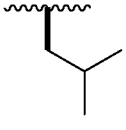 |  | OH | | |
| 3 | Indole | $CH_2CO$ | 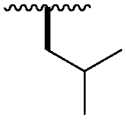 |  | $PhCH_2N$ | | |
| 4 | Indole | CO | 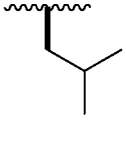 |  | | H | OH |

TABLE I-continued
Compositions used to inhibit 20S proteosome
| # | Ar | $X_3$ | $R_2$ | $R_1$ | $X_1$ | $R_3$ | $X_4$ |
|---|----|-------|-------|-------|-------|-------|-------|
| 5 | Indole | $CH_2CO$ | 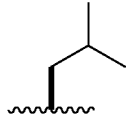 | 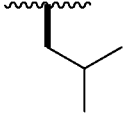 | | H 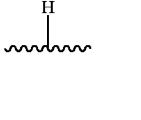 | OH |
| 6 | phenyl | $CH_2CO$ | 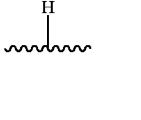 | 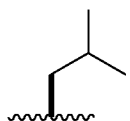 | | H 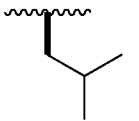 | OH |
| 7 | phenyl | $CH_2CO$ | 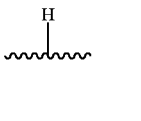 | 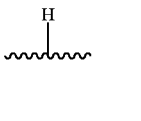 | | H 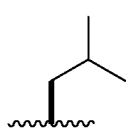 | $PhCH_2N$ |
| 8 | Indole | CO | 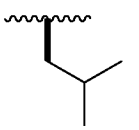 | 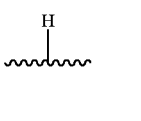 | | H 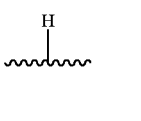 | $PhCH_2N$ |
| 9 | Indole | $CH_2CO$ | 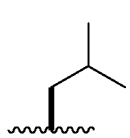 | 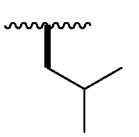 | | H 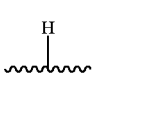 | $PhCH_2N$ |
| 10 | Indole | CO | 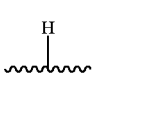 | 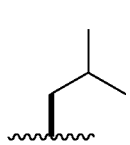 | OH | | |
| 11 | phenyl | CO | 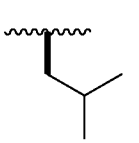 | 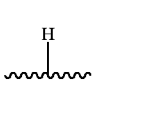 | OH | | |
| 12 | phenyl | CO | 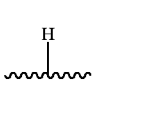 | 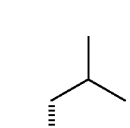 | | H 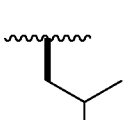 | OH |
| 13 | phenyl | $CH_2CO$ |  | 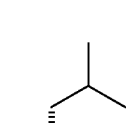 | | 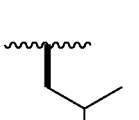 | OH |
| 14 | Indole | CO |  | 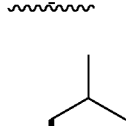 | | 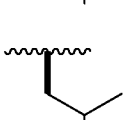 | OH |

TABLE I-continued
Compositions used to inhibit 20S proteosome
| # | Ar | $X_3$ | $R_2$ | $R_1$ | $X_1$ | $R_3$ | $X_4$ |
|---|---|---|---|---|---|---|---|
| 15 | Indole | $CH_2CO$ | 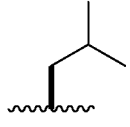 | 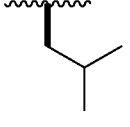 | | 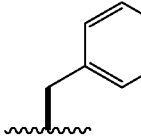 | OH |
| 16 | phenyl | CO | 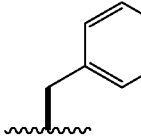 | 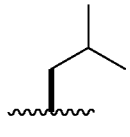 | | 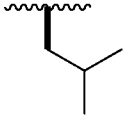 | OH |
| 17 | Indole | $CH_2CO$ | 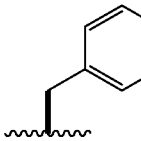 | 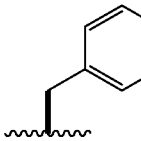 | | 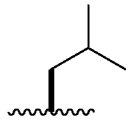 | OH |
| 18 | Indole | $CH_2CO$ | 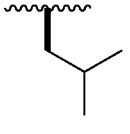 | 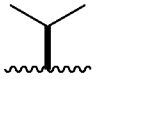 | | 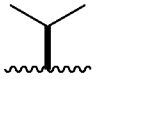 | OH |
| 19 | Indole | $CH_2CO$ | 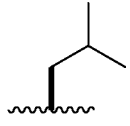 | 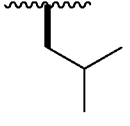 | | 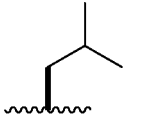 | OH |
| 20 | Indole | $CH_2CO$ | 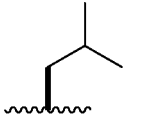 | 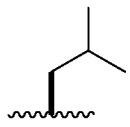 | | 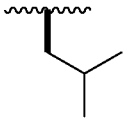 | OH |
| 21 | Indole | $CH_2CO$ | 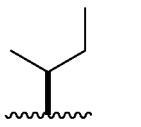 | 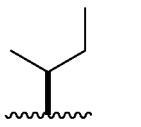 | | 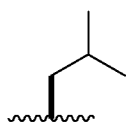 | OH |
| 22 | Indole | $CH_2CO$ | 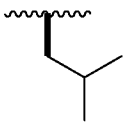 | 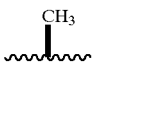 | | 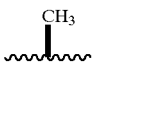 | OH |
| 23 | Indole | $CH_2CO$ | 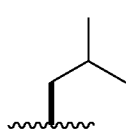 | 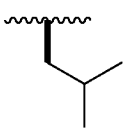 | | 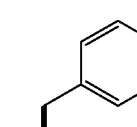 | OH |
| 24 | Indole | $CH_2CO$ | 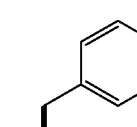 | 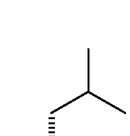 | | 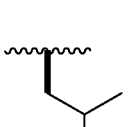 | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 25 | Indole | $CH_2CO$ | isobutyl | isobutyl | | $CH_3$ | OH |
| 26 | Indole | $CH_2CO$ | isobutyl | isobutyl | | 4-hydroxybenzyl | OH |
| 27 | Indole | $CH_2CO$ | isobutyl | isobutyl | | isopropyl | OH |
| 28 | Indole | $CH_2CO$ | isobutyl | isobutyl | | isobutyl | OH |
| 29 | Indole | $CH_2CO$ | isobutyl | isobutyl | | sec-butyl | OH |
| 30 | Indole | $CH_2CO$ | isobutyl | isobutyl | | $CH_3$ | OH |
| 31 | Indole | $CH_2CO$ | isobutyl | isobutyl | | 4-hydroxybenzyl | OH |
| 32 | Indole | $CH_2CO$ | isobutyl | isobutyl | | isopropyl | OH |
| 33 | Indole | $CH_2CO$ | isobutyl | isobutyl | | isobutyl | OH |
| 34 | Indole | $CH_2CO$ | isobutyl | isobutyl | | sec-butyl | OH |

TABLE I-continued

Compositions used to inhibit 20S proteosome

| # | Ar | $X_3$ | $R_2$ | $R_1$ | $X_1$ | $R_3$ | $X_4$ |
|---|---|---|---|---|---|---|---|
| 35 | Indole | $CH_2CO$ | isobutyl | isobutyl | | $CH_3$ | OH |
| 36 | Indole | $CH_2CO$ | isobutyl | isobutyl | | 4-hydroxybenzyl | OH |
| 37 | Indole | $CH_2CO$ | H | isobutyl | | isopropyl | OH |
| 38 | Indole | $CH_2CO$ | β-Ala | isobutyl | | isopropyl | OH |
| 39 | Indole | $CH_2CO$ | n-pentyl | isobutyl | | isopropyl | OH |
| 40 | Indole | $CH_2CO$ | benzyl | isobutyl | | isopropyl | OH |
| 41 | Indole | $CH_2CO$ | CH(OH)CH₃ | isobutyl | | isopropyl | OH |
| 42 | Indole | $CH_2CO$ | $CH_3$ | isobutyl | | isopropyl | OH |
| 43 | Indole | $CH_2CO$ | $HO_2C$-CH₂ | isobutyl | | isopropyl | OH |
| 44 | Indole | $CH_2CO$ | isopropyl | isobutyl | | isopropyl | OH |

TABLE I-continued
Compositions used to inhibit 20S proteosome
| # | Ar | $X_3$ | $R_2$ | $R_1$ | $X_1$ | $R_3$ | $X_4$ |
|---|---|---|---|---|---|---|---|
| 45 | Indole | $CH_2CO$ | 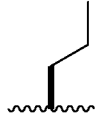 | 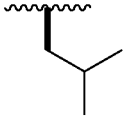 | | 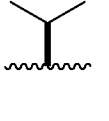 | OH |
| 46 | Indole | $CH_2CO$ | 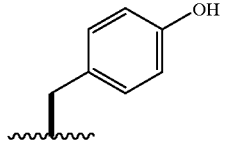 | 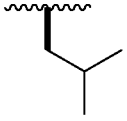 | | 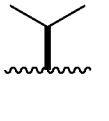 | OH |
| 47 | Indole | $CH_2CO$ | 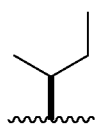 | 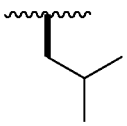 | | 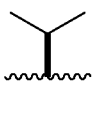 | OH |
| 48 | Indole | $CH_2CO$ | 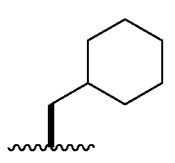 | 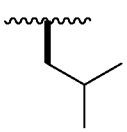 | | 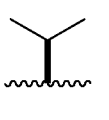 | OH |
| 49 | Indole | $CH_2CO$ | 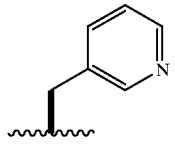 | 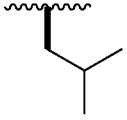 | | 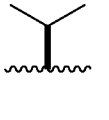 | OH |
| 50 | Indole | $CH_2CO$ | 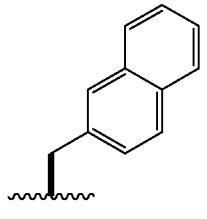 | 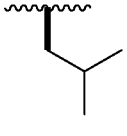 | |  | OH |
| 51 | Indole | $CH_2CO$ | 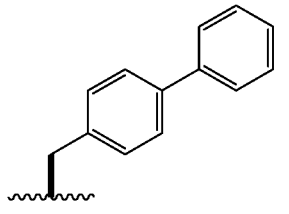 | 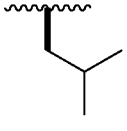 | | 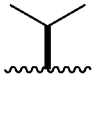 | OH |
| 52 | Indole | $CH_2CO$ |  | 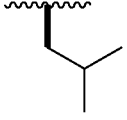 | |  | OH |
| 53 | Indole | $CH_2CO$ | β-Ala | 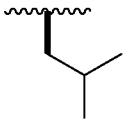 | | 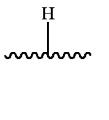 | OH |

TABLE I-continued
Compositions used to inhibit 20S proteosome
| # | Ar | $X_3$ | $R_2$ | $R_1$ | $X_1$ | $R_3$ | $X_4$ |
|---|----|----|----|----|----|----|----|
| 54 | Indole | $CH_2CO$ | 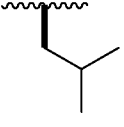 | 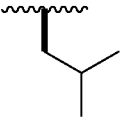 | | H  | OH |
| 55 | Indole | $CH_2CO$ | 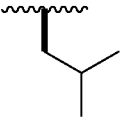 | 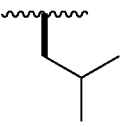 | | H  | OH |
| 56 | Indole | $CH_2CO$ | 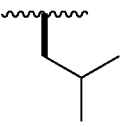 |  | | H  | OH |
| 57 | Indole | $CH_2CO$ | 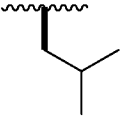 | 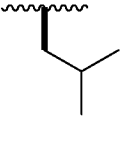 | | H  | OH |
| 58 | Indole | $CH_2CO$ | 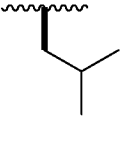 | 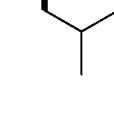 | | H  | OH |
| 59 | Indole | $CH_2CO$ | 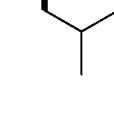 | 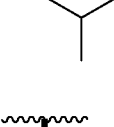 | | H  | OH |
| 60 | Indole | $CH_2CO$ | 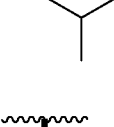 |  | | H  | OH |
| 61 | Indole | $CH_2CO$ |  | 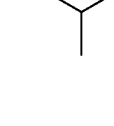 | | H  | OH |
| 62 | Indole | $CH_2CO$ | 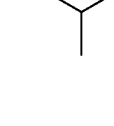 |  | | H  | OH |

TABLE I-continued
Compositions used to inhibit 20S proteosome
| # | Ar | $X_3$ | $R_2$ | $R_1$ | $X_1$ | $R_3$ | $X_4$ |
|---|---|---|---|---|---|---|---|
| 63 | Indole | $CH_2CO$ | 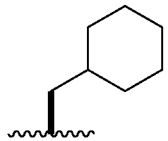 | 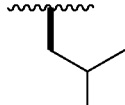 | | H  | OH |
| 64 | Indole | $CH_2CO$ | 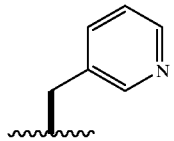 | 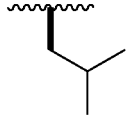 | | H  | OH |
| 65 | Indole | $CH_2CO$ | 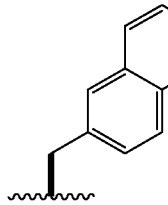 | 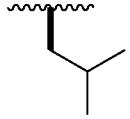 | | H  | OH |
| 66 | Indole | $CH_2CO$ | 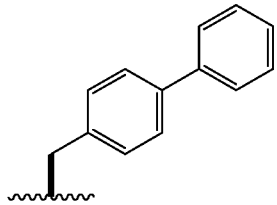 | 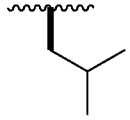 | | H  | OH |
| 67 | Indole | $CH_2CO$ | H  | 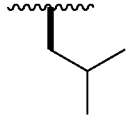 | | $CH_3$  | OH |
| 68 | Indole | $CH_2CO$ | β-Ala | 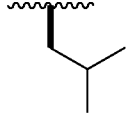 | | $CH_3$  | OH |
| 69 | Indole | $CH_2CO$ | 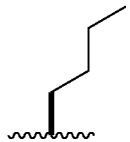 | 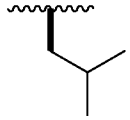 | | $CH_3$  | OH |
| 70 | Indole | $CH_2CO$ | 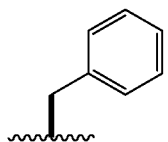 | 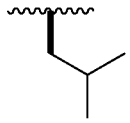 | | $CH_3$  | OH |

TABLE I-continued

Compositions used to inhibit 20S proteosome

| # | Ar | $X_3$ | $R_2$ | $R_1$ | $X_1$ | $R_3$ | $X_4$ |
|---|----|-------|-------|-------|-------|-------|-------|
| 71 | Indole | $CH_2CO$ | CH(OH)– | iBu | | $CH_3$ | OH |
| 72 | Indole | $CH_2CO$ | $CH_3$ | iBu | | $CH_3$ | OH |
| 73 | Indole | $CH_2CO$ | $HO_2C$–$CH_2$– | iBu | | $CH_3$ | OH |
| 74 | Indole | $CH_2CO$ | iPr | iBu | | $CH_3$ | OH |
| 75 | Indole | $CH_2CO$ | n-Pr | iBu | | $CH_3$ | OH |
| 76 | Indole | $CH_2CO$ | 4-HO-benzyl | iBu | | $CH_3$ | OH |
| 77 | Indole | $CH_2CO$ | sec-Bu | iBu | | $CH_3$ | OH |
| 78 | Indole | $CH_2CO$ | cyclohexylmethyl | iBu | | $CH_3$ | OH |
| 79 | Indole | $CH_2CO$ | 3-pyridylmethyl | iBu | | $CH_3$ | OH |

TABLE I-continued
Compositions used to inhibit 20S proteosome
| # | Ar | $X_3$ | $R_2$ | $R_1$ | $X_1$ | $R_3$ | $X_4$ |
|---|---|---|---|---|---|---|---|
| 80 | Indole | $CH_2CO$ | 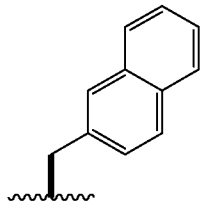 | 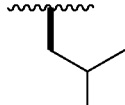 | | $CH_3$  | OH |
| 81 | Indole | $CH_2CO$ | 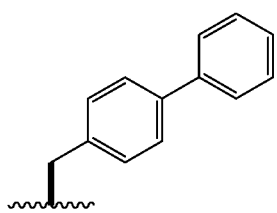 | 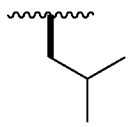 | | $CH_3$  | OH |
| 82 | Indole | $CH_2CO$ | H  | 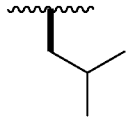 | | 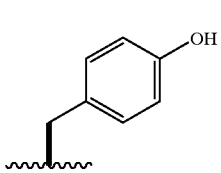 | OH |
| 83 | Indole | $CH_2CO$ | 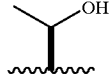 | 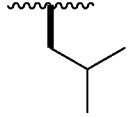 | | 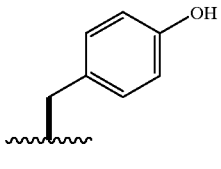 | OH |
| 84 | Indole | $CH_2CO$ | β-Ala | 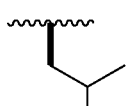 | | 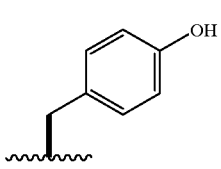 | OH |
| 85 | Indole | CO | 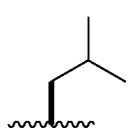 | 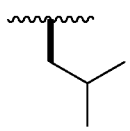 | | H  | OH |
| 86 | Indole | $CH_2CO$ | 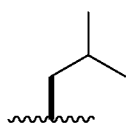 | 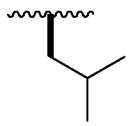 | | H  | OH |
| 87 | Indole | $CH_2CO$ | 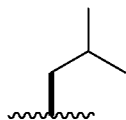 | 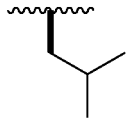 | | 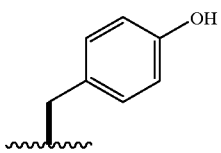 | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 88 | Indole | $CH_2CO$ | isobutyl (stereo) | isobutyl | | 4-hydroxybenzyl | OH |
| 89 | Indole | $CH_2CO$ | H | isobutyl | | $CH_2OH$ | OH |
| 90 | Indole | $CH_2CO$ | β-Ala | isobutyl | | $CH_2OH$ | OH |
| 91 | Indole | $CH_2CO$ | n-pentyl | isobutyl | | $CH_2OH$ | OH |
| 92 | Indole | $CH_2CO$ | benzyl | isobutyl | | $CH_2OH$ | OH |
| 93 | Indole | $CH_2CO$ | CH(OH)CH$_3$ | isobutyl | | $CH_2OH$ | OH |
| 94 | Indole | $CH_2CO$ | $CH_3$ | isobutyl | | $CH_2OH$ | OH |
| 95 | Indole | $CH_2CO$ | $CH_2CO_2H$ | isobutyl | | $CH_2OH$ | OH |
| 96 | Indole | $CH_2CO$ | isopropyl | isobutyl | | $CH_2OH$ | OH |
| 97 | Indole | $CH_2CO$ | n-propyl | isobutyl | | $CH_2OH$ | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 98 | Indole | $CH_2CO$ | 4-hydroxybenzyl | isobutyl | | hydroxymethyl | OH |
| 99 | Indole | $CH_2CO$ | sec-butyl | isobutyl | | hydroxymethyl | OH |
| 100 | Indole | $CH_2CO$ | cyclohexylmethyl | isobutyl | | hydroxymethyl | OH |
| 101 | Indole | $CH_2CO$ | (pyridin-3-yl)methyl | isobutyl | | hydroxymethyl | OH |
| 102 | Indole | $CH_2CO$ | (naphthalen-2-yl)methyl | isobutyl | | hydroxymethyl | OH |
| 103 | Indole | $CH_2CO$ | (biphenyl-4-yl)methyl | isobutyl | | hydroxymethyl | OH |
| 104 | Indole | $CH_2CO$ | H | isobutyl | | benzyl | OH |
| 105 | Indole | $CH_2CO$ | β-Ala | isobutyl | | benzyl | OH |

TABLE I-continued

Compositions used to inhibit 20S proteosome

| # | Ar | $X_3$ | $R_2$ | $R_1$ | $X_1$ | $R_3$ | $X_4$ |
|---|----|-------|-------|-------|-------|-------|-------|
| 106 | Indole | $CH_2CO$ | n-butyl | isobutyl | | benzyl | OH |
| 107 | Indole | $CH_2CO$ | benzyl | isobutyl | | benzyl | OH |
| 108 | Indole | $CH_2CO$ | CH(OH)CH$_3$ | isobutyl | | benzyl | OH |
| 109 | Indole | $CH_2CO$ | CH$_3$ | isobutyl | | benzyl | OH |
| 110 | Indole | $CH_2CO$ | CH$_2$CO$_2$H | isobutyl | | benzyl | OH |
| 111 | Indole | $CH_2CO$ | Val | isobutyl | | benzyl | OH |
| 112 | Indole | $CH_2CO$ | Nva | isobutyl | | benzyl | OH |
| 113 | Indole | $CH_2CO$ | 4-hydroxybenzyl | isobutyl | | benzyl | OH |
| 114 | Indole | $CH_2CO$ | sec-butyl | isobutyl | | benzyl | OH |

TABLE I-continued
Compositions used to inhibit 20S proteosome
| # | Ar | X₃ | R₂ | R₁ | X₁ | R₃ | X₄ |
|---|----|----|----|----|----|----|----|
| 115 | Indole | CH₂CO | 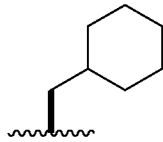 | 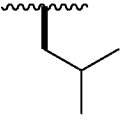 | | 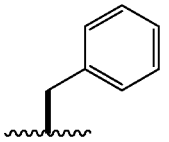 | OH |
| 116 | Indole | CH₂CO | 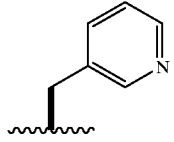 | 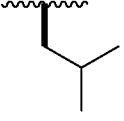 | | 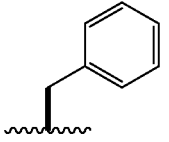 | OH |
| 117 | Indole | CH₂CO | 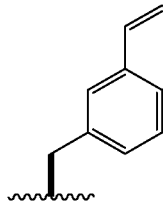 | 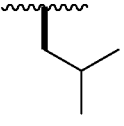 | | 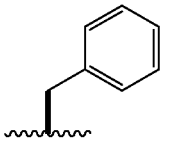 | OH |
| 118 | Indole | CH₂CO | 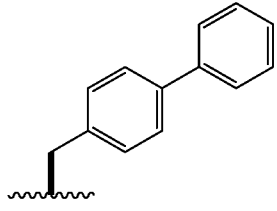 | 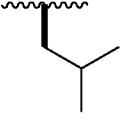 | | 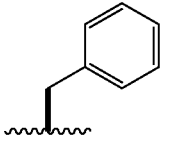 | OH |
| 119 | Indole | CH₂CO | 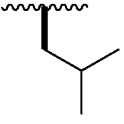 | 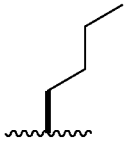 | | 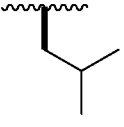 | OH |
| 120 | Indole | CH₂CO | β-Ala | 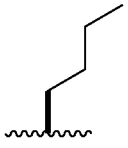 | | 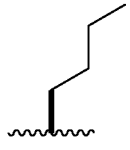 | OH |
| 121 | Indole | CH₂CO | 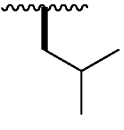 | 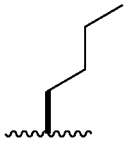 | | 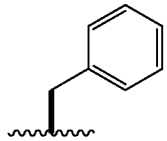 | OH |
| 122 | Indole | CH₂CO | 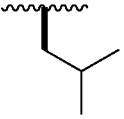 | 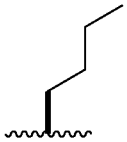 | | | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 123 | Indole | $CH_2CO$ | CH(OH)- | isobutyl | | n-pentyl | OH |
| 124 | Indole | $CH_2CO$ | $CH_3$ | isobutyl | | n-pentyl | OH |
| 125 | Indole | $CH_2CO$ | $HO_2C$-CH$_2$- | isobutyl | | n-pentyl | OH |
| 126 | Indole | $CH_2CO$ | isopropyl | isobutyl | | n-pentyl | OH |
| 127 | Indole | $CH_2CO$ | n-propyl | isobutyl | | n-pentyl | OH |
| 128 | Indole | $CH_2CO$ | 4-hydroxybenzyl | isobutyl | | n-pentyl | OH |
| 129 | Indole | $CH_2CO$ | sec-butyl | isobutyl | | n-pentyl | OH |
| 130 | Indole | $CH_2CO$ | cyclohexylmethyl | isobutyl | | n-pentyl | OH |
| 131 | Indole | $CH_2CO$ | 3-pyridylmethyl | isobutyl | | n-pentyl | OH |

TABLE I-continued
Compositions used to inhibit 20S proteosome
| # | Ar | $X_3$ | $R_2$ | $R_1$ | $X_1$ | $R_3$ | $X_4$ |
|---|----|----|----|----|----|----|----|
| 132 | Indole | $CH_2CO$ | 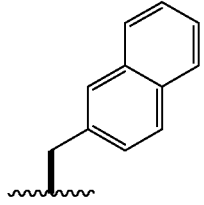 | 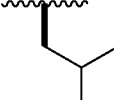 | | 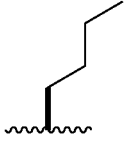 | OH |
| 133 | Indole | $CH_2CO$ | 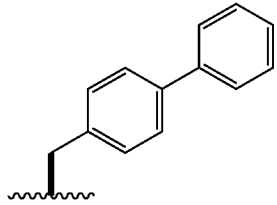 | 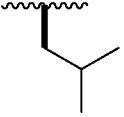 | | 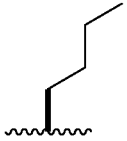 | OH |
| 134 | Indole | $CH_2CO$ | 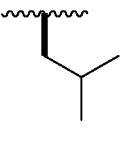 | 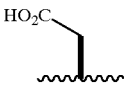 | | 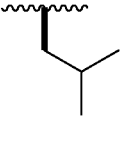 | OH |
| 135 | Indole | $CH_2CO$ | β-Ala | 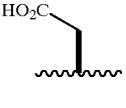 | | 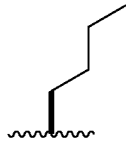 | OH |
| 136 | Indole | $CH_2CO$ | 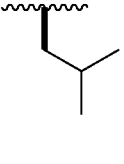 |  | | 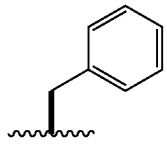 | OH |
| 137 | Indole | $CH_2CO$ | 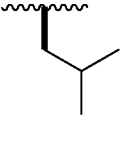 |  | | 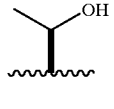 | OH |
| 138 | Indole | $CH_2CO$ | 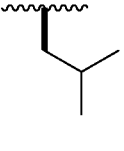 | 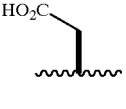 | |  | OH |
| 139 | Indole | $CH_2CO$ | 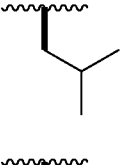 | 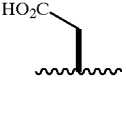 | | 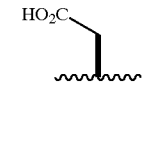 | OH |
| 140 | Indole | $CH_2CO$ | 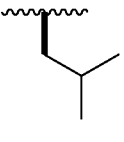 | 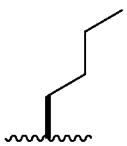 | | | OH |

TABLE I-continued
Compositions used to inhibit 20S proteosome
| # | Ar | $X_3$ | $R_2$ | $R_1$ | $X_1$ | $R_3$ | $X_4$ |
|---|----|-------|-------|-------|-------|-------|-------|
| 141 | Indole | $CH_2CO$ |  | 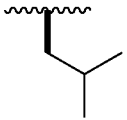 | | 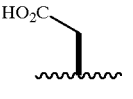 $HO_2C$ | OH |
| 142 | Indole | $CH_2CO$ | 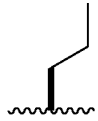 | 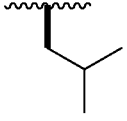 | | 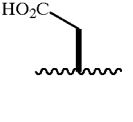 $HO_2C$ | OH |
| 143 | Indole | $CH_2CO$ | 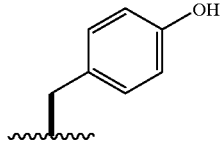 OH | 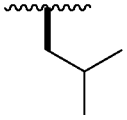 | | 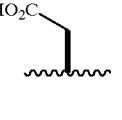 $HO_2C$ | OH |
| 144 | Indole | $CH_2CO$ | 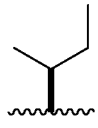 | 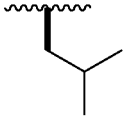 | | 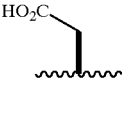 $HO_2C$ | OH |
| 145 | Indole | $CH_2CO$ | 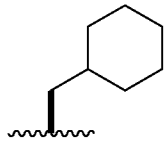 | 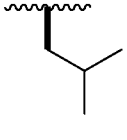 | | 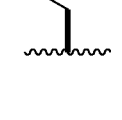 $HO_2C$ | OH |
| 146 | Indole | $CH_2CO$ | 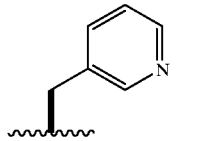 | 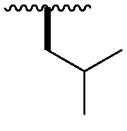 | | 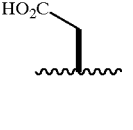 $HO_2C$ | OH |
| 147 | Indole | $CH_2CO$ | 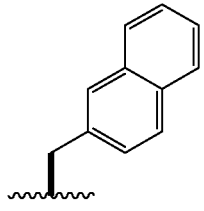 | 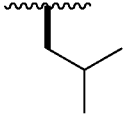 | | 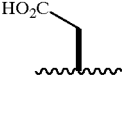 $HO_2C$ | OH |
| 148 | Indole | $CH_2CO$ | 4,4'-BPA | 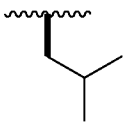 | | 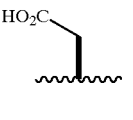 $HO_2C$ | OH |
| 149 | Indole | $CH_2CO$ | H 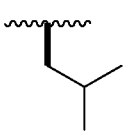 | 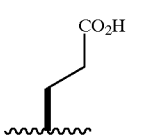 | | $CO_2H$ | OH |

TABLE I-continued

Compositions used to inhibit 20S proteosome

| # | Ar | $X_3$ | $R_2$ | $R_1$ | $X_1$ | $R_3$ | $X_4$ |
|---|---|---|---|---|---|---|---|
| 150 | Indole | $CH_2CO$ | β-Ala | isobutyl | | $CH_2CH_2CO_2H$ | OH |
| 151 | Indole | $CH_2CO$ | n-butyl | isobutyl | | $CH_2CH_2CO_2H$ | OH |
| 152 | Indole | $CH_2CO$ | benzyl | isobutyl | | $CH_2CH_2CO_2H$ | OH |
| 153 | Indole | $CH_2CO$ | CH(OH)CH$_3$ | isobutyl | | $CH_2CH_2CO_2H$ | OH |
| 154 | Indole | $CH_2CO$ | CH$_3$ | isobutyl | | $CH_2CH_2CO_2H$ | OH |
| 155 | Indole | $CH_2CO$ | CH$_2$CO$_2$H | isobutyl | | $CH_2CH_2CO_2H$ | OH |
| 156 | Indole | $CH_2CO$ | isopropyl | isobutyl | | $CH_2CH_2CO_2H$ | OH |
| 157 | Indole | $CH_2CO$ | n-propyl | isobutyl | | $CH_2CH_2CO_2H$ | OH |
| 158 | Indole | $CH_2CO$ | 4-hydroxybenzyl | isobutyl | | $CH_2CH_2CO_2H$ | OH |
| 159 | Indole | $CH_2CO$ | sec-butyl | isobutyl | | $CH_2CH_2CO_2H$ | OH |

TABLE I-continued
Compositions used to inhibit 20S proteosome
| # | Ar | $X_3$ | $R_2$ | $R_1$ | $X_1$ | $R_3$ | $X_4$ |
|---|---|---|---|---|---|---|---|
| 160 | Indole | $CH_2CO$ | 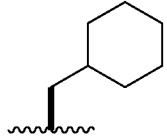 | 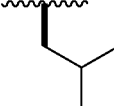 | | 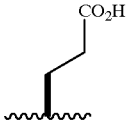 $CO_2H$ | OH |
| 161 | Indole | $CH_2CO$ | 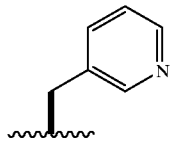 | 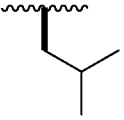 | | 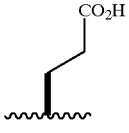 $CO_2H$ | OH |
| 162 | Indole | $CH_2CO$ | 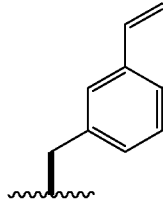 | 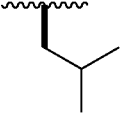 | | 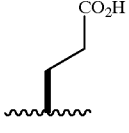 $CO_2H$ | OH |
| 163 | Indole | $CH_2CO$ | 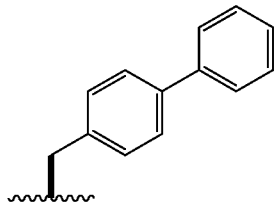 | 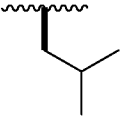 | | 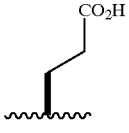 $CO_2H$ | OH |
| 164 | Indole | $CH_2CO$ | 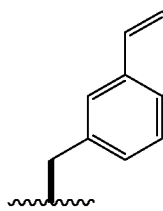 | 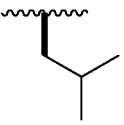 | | 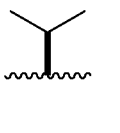 | OH |
| 165 | Indole | $CH_2CO$ | 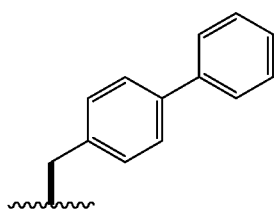 | 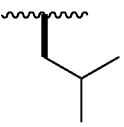 | | 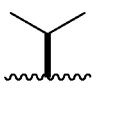 | OH |
| 167 | Indole | $CH_2CO$ | 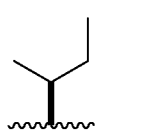 | 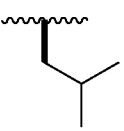 | | 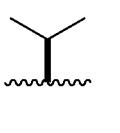 | OH |
| 168 | Indole | $CH_2CO$ | 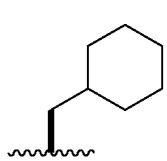 | 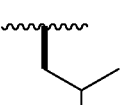 | | 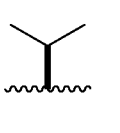 | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 169 | Indole | $CH_2CO$ | 3-pyridylmethyl | isobutyl | | isopropyl | OH |
| 170 | Indole | $CH_2CO$ | 2-naphthylmethyl | isobutyl | | isopropyl | OH |
| 171 | Indole | $CH_2CO$ | 4-biphenylmethyl | isobutyl | | H | OH |
| 172 | Indole | $CH_2CO$ | cyclohexylmethyl | isobutyl | | isopropyl | OH |
| 173 | Indole | $CH_2CO$ | 3-pyridylmethyl | isobutyl | | isopropyl | OH |
| 174 | Indole | $CH_2CO$ | 4-biphenylmethyl | isobutyl | | n-butyl | OH |
| 175 | Indole | $CH_2CO$ | 4-biphenylmethyl | isobutyl | | benzyl | OH |

TABLE I-continued

Compositions used to inhibit 20S proteosome

| # | Ar | $X_3$ | $R_2$ | $R_1$ | $X_1$ | $R_3$ | $X_4$ |
|---|---|---|---|---|---|---|---|
| 176 | Indole | $CH_2CO$ | 4-phenylbenzyl | isobutyl | | $HO_2C$-$CH_2$- | OH |
| 177 | Indole | $CH_2CO$ | 4-phenylbenzyl | isobutyl | | $-CH_2CH_2CO_2H$ | OH |
| 178 | Indole | $CH_2CO$ | 2-naphthylmethyl | isobutyl | | n-butyl | OH |
| 179 | Indole | $CH_2CO$ | 2-naphthylmethyl | isobutyl | | benzyl | OH |
| 180 | Indole | $CH_2CO$ | 2-naphthylmethyl | isobutyl | | $HO_2C$-$CH_2$- | OH |
| 181 | Indole | $CH_2CO$ | 2-naphthylmethyl | isobutyl | | $-CH_2CH_2CO_2H$ | OH |
| 182 | Indole | $CH_2CO$ | isobutyl | | benzyl | OH | |

TABLE I-continued

Compositions used to inhibit 20S proteosome

| # | Ar | $X_3$ | $R_2$ | $R_1$ | $X_1$ | $R_3$ | $X_4$ |
|---|---|---|---|---|---|---|---|
| 183 | Indole | $CH_2CO$ | H | H | | H | OH |
| 184 | Indole | $CH_2CO$ | H | isobutyl | | H | OH |
| 185 | Indole | $CH_2CO$ | 4-biphenylmethyl | isobutyl | | $H_2NOC$-$CH_2$ | OH |
| 186 | Indole | $CH_2CO$ | 4-biphenylmethyl | isobutyl | | $CH_2CH_2CONH_2$ | OH |
| 187 | Indole | $CH_2CO$ | 4-biphenylmethyl | isobutyl | | 4-biphenylmethyl | OH |
| 188 | Indole | $CH_2CO$ | 4-biphenylmethyl | isobutyl | | β-Alanine | OH |
| 189 | Indole | $CH_2CO$ | 4-biphenylmethyl | isobutyl | | 4-biphenylmethyl | OH |

TABLE I-continued

Compositions used to inhibit 20S proteosome

| # | Ar | $X_3$ | $R_2$ | $R_1$ | $X_1$ | $R_3$ | $X_4$ |
|---|----|-------|-------|-------|-------|-------|-------|
| 190 | Indole | $CH_2CO$ | 4-biphenylmethyl | isobutyl | | 4-imidazolylmethyl | OH |
| 191 | Indole | $CH_2CO$ | 4-biphenylmethyl | isobutyl | | 3-guanidinopropyl | OH |
| 192 | Indole | $CH_2CO$ | 4-biphenylmethyl | isobutyl | | 3-pyridylmethyl | OH |
| 193 | Indole | $CH_2CO$ | 4-biphenylmethyl | isobutyl | | 4-aminobutyl | OH |
| 194 | Indole | $CH_2CO$ | 4-biphenylmethyl | isobutyl | | phenyl | OH |
| 195 | Indole | $CH_2CO$ | 4-biphenylmethyl | isobutyl | | carboxymethyl | OH |

TABLE I-continued

Compositions used to inhibit 20S proteosome

| # | Ar | $X_3$ | $R_2$ | $R_1$ | $X_1$ | $R_3$ | $X_4$ |
|---|----|----|----|----|----|----|----|
| 196 | Indole | $CH_2CO$ | 4-phenylbenzyl | isobutyl | | imidazol-4-ylmethyl | OH |
| 197 | Indole | $CH_2CO$ | 4-phenylbenzyl | isobutyl | | 3-guanidinopropyl | OH |
| 198 | Indole | $CH_2CO$ | 4-phenylbenzyl | isobutyl | | thiazol-4-ylmethyl | OH |
| 199 | Indole | $CH_2CO$ | n-propyl | isopropyl | | isopropyl | OH |
| 200 | Indole | $CH_2CO$ | carboxymethyl | isobutyl | | isopropyl | OH |
| 201 | Indole | $CH_2CO$ | n-propyl | isobutyl | | isopropyl | OH |
| 202 | Indole | $CH_2CO$ | 4-hydroxybenzyl | isopropyl | | isopropyl | OH |
| 203 | Indole | $CH_2CO$ | isopropyl | isopropyl | | isopropyl | OH |

TABLE I-continued

Compositions used to inhibit 20S proteosome

| # | Ar | $X_3$ | $R_2$ | $R_1$ | $X_1$ | $R_3$ | $X_4$ |
|---|---|---|---|---|---|---|---|
| 204 | Indole | $CH_2CO$ | 2-naphthylmethyl | isobutyl | | 4-imidazolylmethyl (H on N) | OH |
| 205 | Indole | $CH_2CO$ | 2-naphthylmethyl | isobutyl | | 3-guanidinopropyl | OH |
| 206 | Indole | $CH_2CO$ | 2-naphthylmethyl | isobutyl | | 3-pyridylmethyl | OH |
| 207 | Indole | $CH_2CO$ | β-Alanine | | β-Alanine | | OH |

The compounds described above are useful for treating diseases and disorders mediated by the 20S proteosome such as antiproliferative diseases, cancer, inflammation. It is preferred that the compositions of this invention are used to treat antiproliferative disorders and inflammation. It is most preferred that the compounds of this invention are used to treat inflammatory diseases.

The compounds of the present invention are useful for treating disorders mediated by 20S proteasome in mammals.

The compounds of this invention may be administered to mammals both prophylactically and therapeutically by any administration protocol that is capable of supplying at least one compound of this invention to a 20S proteasome. Non-limiting examples of useful administration protocols include orally, parenterally, dermally, transdermally, rectally, nasally or by any other suitable pharmaceutical composition administration protocol that is within the knowledge of one skilled in the art.

The compositions of this invention may be administered in suitable pharmaceutical dosage forms. The pharmaceutical dosage form will depend largely upon the administration protocol used. The term pharmaceutical dosage form refers to items such as tablets, capsules, liquids and powders, comprising 20S proteasome inhibitors of this invention alone or in the presence of one or more pharmaceutical excipients. The choice of additives such as excipients and adjuvants again will depend largely upon the chosen administration protocol. Those skilled in the pharmaceutical arts will recognize a wide variety of formulations and vehicles for administering compositions of this invention.

The administration protocol chosen for compounds of this invention will ultimately dictate the final form and composition of pharmaceutical dosage forms comprising the 20S proteasome inhibitors of this invention. For example, internal administration of compounds of this invention is effected, orally, in the form of powders, tablets, capsules, pastes, drinks, granules, or solutions, suspensions and emulsions which can be administered orally, or bolus, in medicated food, or in drinking water. Internal administration may also be accomplished using a timed release formulation including additives such as surfactant or starch coated capsules, or using a quick release formulation such as a freeze-dried fast dissolving tablet. Dermal administration is effected, for example, in the form of transdermal patches, spraying or pouring-on and spotting-on. Parenteral administration is effected, for example, in the form of injection (intramuscularly, subcutaneously, intravenously, intraperitoneally) or by implants.

Suitable pharmaceutical dosage forms incorporating the 20S proteasome inhibitors of this invention include but are not limited to solutions such as solutions for injection, oral solutions, concentrates for oral administration after dilution, solutions for use on the skin or in body cavities, pour-on and spot-on formulations, gels; emulsions and suspension for oral or dermal administration and for injection; semi-solid preparations; formulations in which the active compound is incorporated in cream base or in an oil-in-water or water-in-oil emulsion base; solid preparations such as powders, premixes or concentrates, granules, pellets, tablets, boli, capsules; aerosols and inhalants, and shaped articles containing active compound.

Pharmaceutical dosage forms that are solutions may be administered by injection intravenously, intramuscularly and subcutaneously. Solutions for injection are prepared by dissolving the active compound in a suitable solvent and, if appropriate, adding adjuvants such as solubilizers, acids, bases, buffer salts, antioxidants and preservatives. The solutions are sterile-filtered and drawn off.

Alternatively, solutions including compositions of this invention may be administered orally. Concentrates of compositions of this invention are preferably administered orally only after diluting the concentrate to the administration concentration. Oral solutions and concentrates are prepared as described above in the case of the solutions for injection. Solutions for use on the skin are applied dropwise, brushed on, rubbed in, splashed on or sprayed on. These solutions are prepared as described above in the case of solutions for injection.

Gels are applied to the skin, or introduced into body cavities. Gels are prepared by treating solutions which have been prepared as described in the case of the solutions for injection with such an amount of thickener that a clear substance of cream-like consistency is formed, or by any other means known to one skilled in the art.

Pour-on and spot-on formulations are poured onto, or splashed onto, limited areas of the skin, the active compound penetrating the skin and acting systemically. Pour-on and spot-on formulations are prepared by dissolving, suspending or emulsifying the active compound in suitable solvents or solvent mixtures which are tolerated by the skin. If appropriate, other adjuvants such as colorants, resorption accelerators, antioxidants, light stabilizers, and tackifiers are added.

Emulsions can be administered orally, dermally or in the form of injections. Emulsions are either of the water-in-oil type or of the oil-in-water type. They are prepared by dissolving 20S proteasome inhibitors either in the hydrophobic or in the hydrophilic phase and homogenizing the phase with a solvent of the opposite phase with the aid of suitable adjuvants such as emulsifiers, colorants, resorption accelerators, preservatives, antioxidants, light stabilizers, and viscosity-increasing substances.

Suspensions can be administered orally, dermally or in the form of injection. They are prepared by suspending the active compound in a liquid if appropriate with the addition of further adjuvants such as wetting agents, colorants, resorption accelerators, preservatives, antioxidants and light stabilizers.

The pharmaceutical compositions of this invention may include one or more additives in the form of pharmaceutically acceptable additives. Useful additives include solvents, solubilizers, preservatives, thickeners, wetting agents, colorants, resorption accelerators, antioxidants, light stabilizers, tackifiers, viscosity increasing substances, fillers, flavorings, lubricating agents, and any other pharmaceutical composition additive known to those skilled in the art.

The additive may be a solvent such as water, alcohols such as ethanol, butanol, benzyl alcohol, glycerol, propylene glycol, polyethylene glycols, N-methyl-pyrrolidone, alkanols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol mono-methyl ether, diethylene glycol mono-butyl ether, ketones such as acetone, methyl ethyl ketone, aromatic and/or aliphatic hydrocarbons, vegetable or synthetic oils, DMF, dimethylacetamide, N-methyl-pyrrolidone, 2,2-dimethyl-4-oxy-methylene-1,3-dioxolane.

The following additives may be useful as solubilizers of the compositions of this invention: solvents which enhance solution of the active compound in the main solvent or which prevent its precipitation. Examples are polyvinylpyrrolidone, polyoxyethylated castor oil, polyoxyethylated sorbitan esters.

Useful preservatives are, for example, benzyl alcohol, trichlorobutanol, p-hydroxybenzoic esters, and n-butanol.

Useful thickeners include inorganic thickeners such as bentonite, colloidal silica, aluminum monostearate, organic thickeners such as cellulose derivatives, polyvinyl alcohols and their copolymers, acrylates and methacrylates.

Other liquids which may be useful in pharmaceutical dosage forms of this invention are, for example, homogeneous solvents, solvent mixtures, and wetting agents which are typically surfactants.

Useful colorants are all colorants which are non-toxic and which can be dissolved or suspended.

Useful resorption accelerators are DMSO, spreading oils such as isopropyl myristate, dipropylene glycol pelargonate, silicone oils, fatty acid esters, triglycerides, fatty alcohols.

Useful antioxidants are sulphites or metabisulphites such as potassium metabisulphite, ascorbic acid, butylhydroxytoluene, butylhydroxyanisole, tocopherol.

A useful light stabilizer is novantisolic acid.

Useful tackifiers include cellulose derivatives, starch derivatives, polyacrylates, natural polymers such as alginates, gelatin.

Useful emulsifiers include non-ionic surfactants such as polyoxyethylated castor oil, polyoxyethylated sorbitan monooleate, sorbitan monostearate, glycerol monostearate, polyoxyethyl stearate, alkylphenol polyglycol ethers; ampholytic surfactants such as Di-Na N-lauryl-beta-iminodipropionate or lecithin; anionic surfactants, such as Na-lauryl sulphate, fatty alcohol ether sulphates, the monoethanolamine salt of mono/dialkylpolyglycol ether orthophosphoric esters; cationic surfactants such as cetyltrimethylammonium chloride.

Useful viscosity-increasing substances and substances which stabilize a therapeutic emulsion include carboxymethylcellulose, methylcellulose and other cellulose and starch derivatives, polyacrylates, alginates, gelatin, gum Arabic, polyvinylpyrrolidone, polyvinyl alcohol, copolymers of methyl vinyl ether and maleic anhydride, polyethylene glycols, waxes, colloidal silica or mixtures of the substances mentioned.

To prepare solid pharmaceutical dosage forms, the active compound is mixed with suitable additives, if appropriate with the addition of adjuvants, and the mixture is formulated as desired. Examples of physiologically acceptable solid inert additives include sodium chloride, carbonates such as calcium carbonate, hydrogen carbonates, aluminum oxides, silicas, clays, precipitated or colloidal silicon dioxide, and phosphates. Examples of solid organic additives include sugars, cellulose, foods such as dried milk, animal meals, cereal meals and coarse cereal meals and starches. Other suitable additives include lubricants and gliding agents such as magnesium stearate, stearic acid, talc, bentonites; disintegrants such as starch or crosslinked polyvinylpyrrolidone; binders such as, starch, gelatin or linear polyvinylpyrrolidone; and dry binders such as microcrystalline cellulose.

In the pharmaceutical dosage forms described herein, the active compounds can be present in the form of a mixture with at least one other 20S proteasome inhibitor. Alternatively, or in addition, the pharmaceutical dosage forms of the invention can, in addition to at least one 20S proteasome inhibitor, include any pharmaceutical compound that is capable of treating any known malady or disorder where the administration of both together create no unacceptable adverse effects.

Methods for treating 20S proteasome mediated diseases and disorders comprises the administration of an effective quantity of the chosen compound or combinations thereof, preferably dispersed in a pharmaceutical dosage form. Ready-to-use pharmaceutical dosage forms of this invention contain the active compound in concentrations of from 10 ppm to 20 percent by weight, and preferably of from 0.1 to 10 percent by weight. Pharmaceutical dosage forms of this invention that are diluted prior to administration, preferably contain the active compound in concentrations of from 0.5 to 90 percent by weight, and preferably of from 5 to 50 percent by weight. In general, it has proved advantageous to administer amounts of approximately 0.01 mg to approximately 100 mg of active compound per kg of body weight per day to achieve effective results.

The amount and frequency of administration of pharmaceutical dosage forms comprising 20S proteasome inhibitors of this invention will be readily determined by one skilled in the art depending upon, among other factors, the route of administration, age and condition of the patient. These dosage units may be administered one to ten times daily for acute or chronic disease. No unacceptable toxicological effects are expected when compounds of the invention are administered in accordance with the present invention.

The pharmaceutical dosage forms comprising 20S proteasome inhibitors of this invention are made following the conventional techniques of pharmacy involving milling, mixing, granulation, and compressing, when necessary, for tablet forms; or milling, mixing and filling for hard gelatin capsule forms. When a liquid additive is used, the preparation will be in the form of a syrup, elixir, emulsion or an aqueous or non-aqueous suspension. Such a liquid formulation may be administered directly p.o. or filled into a soft gelatin capsule.

While the compositions described herein may be administered as described above, it is preferred that the method of this invention is achieved by administering the compound described herein orally. When the oral administration route is chosen, a larger quantity of reactive agent will be required to produce the same effect as a smaller quantity given for example parenterally. In accordance with good clinical practice, it is preferred to administer the compound according to this method at a concentration level that would produce effective therapeutic results without causing any harmful side effects.

The compositions of this invention have non-therapeutic utility as well. The compositions of this invention are useful as analytical standards for 20S proteasome inhibitor assays.

Example 1

The compounds useful in the therapeutic method of this invention are prepared by conventional methods of organic chemistry. References that may be consulted in describing the art of the synthesis of these compounds include Bodansky's "The Practice of Peptide Synthesis," Springer-Verlag, First Edition, 1984; "Protective Groups in Organic Synthesis," Second Edition, John Wiley and Sons, New York, 1991. All peptide couplings are accomplished at room temperature with gentle and constant agitation. Peptide couplings and deprotections are monitored using the Kaiser test for amines. Xaa refers to any of the commerically available amino acids that may be purchased pre-attached to the MBHA resin. Yaa and Zaa refer to any of the commerically available amino acids.

The compounds of this invention may be prepared by solid phase peptide synthesis (SPPS) in the general procedure that follows: Xaa-MBHA-resin is weighed and transferred to a syringe equipped with a fritted filter. The resin is pre-swollen in DMF and then the N-terminal protecting group is removed by treatment with 30%, piperidine in DMF for 30 minutes. The deprotection solution is removed. The deprotected resin is washed five times with DMF, five times with MeOH, and then five times with DMF. Amino acid Yaa may then be coupled to the deprotected resin using a solution of Yaa in DMF containing 3 equivalents each of Yaa, carbodiimide coupling reagent and HOBT (hydroxy benzotriazole). Succesive couplings with solutions of Yaa may be necessary to achieve coupling efficiencies that pass the Kaiser test. The N-terminal group deprotection and Yaa coupling step may be repeated to couple a third amino acid Zaa. The final coupling step uses ketoacid, carbodiimide, and HOBT in DMF, and this step is repeated until the coupling passes the Kaiser test. The completed peptide sequence on resin is dried under vacuum for at least six hours and then cleaved by treatment for 2.5 hours with either 95/5 trifluoroacetic acid/water or a freshly prepared solution of 90%, trifluoroacetic acid, 3% ethanedithiol, 5% thioanisole, and 2% anisole. The cleaved products are recovered by either lyophillization from water or trituration from diethyl ether. Product purities are estimated from TLC. Selected peptide samples are checked by $^1$H NMR to confirm product identity.

Example 2

In this Example (3'-Indolepyruvic acid)-N-biphenylalanine-D-Leu-Asp-OH was prepared according to the method of Example 1.

Fmoc-N-Asp(Ot-Bu)-MBHA-resin (20 mg) is weighed and transferred to a syringe equipped with a fritted filter. The resin is pre-swollen in 1 mL DMF for 30 minutes. The Fmoc (fluorenylmethyloxycarbonyl) protecting group is removed by treatment with 20% piperidine in DMF for 30 minutes. The deprotection solution is removed. The deprotected resin is washed five times with DMF, five times with MeOH, and then five times with DMF. Fmoc-D-Leu-OH is coupled to the deprotected resin (1 eq) using a solution of Fmoc-D-Leu-OH (3 eq) in 1 mL DMF containing carbodiimide (3 eq) and HOBT (hydroxy benzotriazole) (3 eq). A second or third coupling with solutions of Fmoc-D-Leu-OH may be necessary to achieve coupling efficiencies that pass the Kaiser test. The Fmoc deprotection and amino acid coupling step are repeated to couple Fmoc-N-(4,4-biphenyl)alanine. The final coupling step uses indolepyruvic acid (5 eq), diisopropylcarbodiimide (5 eq), and HOBT (5 eq) in DMF, and this step is repeated until the coupling passes the Kaiser test. The completed peptide sequence on resin is dried under vacuum for at least six hours and then cleaved by treatment for 2.5 hours with 1 mL of either 95/5 trifluoroacetic acid/water or a freshly prepared solution of 90% trifluoroacetic acid, 5% thioanisole, 3% ethanedithiol, and 2% anisole. The cleaved products are recovered by either lyophillization from water or trituration from diethyl ether. Product purities are estimated from TLC.

$^1$H NMR (400 MHz, d$_6$-DMSO): δ 6.5–7.7 (m, 14H), 4.5 (m, 1H), 4.1(m, 2H), 3.4(m, 2H), 3 (m, H), 2.7 (m, 1H), 1.1–1.5 (m, 3H), 0.5–0.9 (m, 6H).

Example 3

In this example, (3'-Indolepyruvic acid)-N-biphenylalaanine-D-Leu-Asp-OH was prepared using Chiron Mimotopes Pin Technology The first amino acid residue Xaa is attached to 4-(hydroxymethyl)phenoxyacetamido handle) resin pins (5.7 μmole/pin) by coupling each pin in 800 μL of coupling solution (100 mM amino acid, 100 mM DIC, 10 mM DMAP, ¼ DMF/CH$_2$Cl$_2$) for two hours. The pins are then rinsed with a 5 min DMF wash, two 5 min MeOH washes, and 15 minutes of air drying. Deprotection of the Fmoc group is carried out for 30 min with 800 μL 20% piperidine in DMF. Repeat pin washings (1 DMF wash, 2 MEOH washes, 15 minutes air drying). The second amino acid residue Yaa was coupled (100 mM Yaa, 100 mM DIC, 100 mM HOBT, and bromophenol blue indicator in DMF) until the blue color no longer adheres to the pin surface. The coupling was repeated as necessary. The rinse cycle and Fmoc deprotection washes were then repeated as well. The next amino acid, Zaa, was coupled by repeating the coupling and washing procedures for coupling Yaa, repeating the coupling if necessary. The last residue, indolepyruvic acid is coupled with 15 eq, 100 mM, 15 eq DIC, 15 eq HOBT, and bromophenol blue indicator in DMF. Repeat coupling if necessary. After the last wash, the orange pins were removed from their supports and cleaved in individual 2 mL plastic centrifuge tubes with 1.5 mL of a freshly prepared solution of 90%, trifluoroacetic acid, 5% thioanisole, 3% ethanedithiol, and 2% anisole for 2.5 hours. The pins were removed from the tubes and the mixture was blown to near dryness under a nitrogen stream. Triturate with Et$_2$O and spin down each tube. This step was repeated three times per tube. The precipitated peptides were collected, lyophillized, weighed, and used. Product purity was estimated by TLC. Initial products were cospotted and checked against authentic samples obtained in Example 1.

Example 4

Compounds of this invention prepared according to the method of Example 1 were tested as follows. The 20S catalytic subunit of the proteasome (also known as the multicatalytic proteinase complex) was purified to homogeneity from bovine brain according to published methods (Wilk S. and Orlowski, M 1983, 40 842 J.Neurochem). The chymotryptic activity of the complex is measured by the increase in fluorescence following cleavage of the substrate peptide succinyl-leucine-leucine-valine-tyrosine-7-amino-4methyl coumarin. The standard in vitro assay consists of 2 μg 20S proteasome, 0.1–100 μg/ml proteasome inhibitor in 200 μl 50 mM HEPES, containing 0.1% sodium dodecyl sulphate, pH 7.5. The proteolytic reaction is initiated by the addition of 50 μM flourogenic peptide substrate and allowed to progress for 15 minutes at 37° C. The reaction is terminated by the addition of 100 μL of 100 mM acetate buffer, pH 4.0. The rate of proteolysis is directly proportional to the amount of liberated aminomethylcoumarin which is measured by fluorescent spectroscopy (EX 370 nm, EM 430 nm).

The results of the 20S proteasome inhibitor assays are presented in Table II.

TABLE II

IC 50 values for the inhibition of the chymotrypsin-like activity of 20S proteasome.

| Compound # | IC$_{50}$ μg/mL |
| --- | --- |
| 1 | 10 |
| 2 | 10 |
| 3 | >10 |
| 4 | 10 |
| 5 | >10 |
| 6 | >10 |

TABLE II-continued

IC 50 values for the inhibition of the chymotrypsin-like activity of 20S proteasome.

| Compound # | IC$_{50}$ μg/mL |
| --- | --- |
| 7 | >10 |
| 8 | >10 |
| 9 | >10 |
| 10 | >10 |
| 11 | >10 |
| 12 | >10 |
| 13 | >10 |
| 14 | >10 |
| 15 | 10 |
| 16 | 10 |
| 17 | >10 |
| 18 | >10 |
| 19 | >10 |
| 20 | >10 |
| 21 | >10 |
| 22 | >10 |
| 23 | >10 |
| 24 | >10 |
| 25 | >10 |
| 26 | >10 |
| 27 | >10 |
| 28 | >10 |
| 29 | >10 |
| 30 | >10 |
| 31 | >10 |
| 32 | >10 |
| 33 | >10 |
| 34 | >10 |
| 35 | >10 |
| 36 | >10 |
| 37 | >10 |
| 38 | >10 |
| 39 | >10 |
| 40 | >10 |
| 41 | >10 |
| 42 | >10 |
| 43 | >10 |
| 44 | >10 |
| 45 | >10 |
| 46 | >10 |
| 47 | >10 |
| 48 | >10 |
| 49 | >10 |
| 50 | >10 |
| 51 | >10 |
| 52 | >10 |
| 53 | >10 |
| 54 | >10 |
| 55 | >10 |
| 56 | >10 |
| 57 | >10 |
| 58 | >10 |
| 59 | >10 |
| 60 | >10 |
| 61 | >10 |
| 62 | >10 |
| 63 | >10 |
| 64 | >10 |
| 65 | >10 |
| 66 | >10 |
| 67 | >10 |
| 68 | >10 |
| 69 | >10 |
| 70 | >10 |
| 71 | >10 |
| 72 | >10 |
| 73 | >10 |
| 74 | >10 |
| 75 | >10 |
| 76 | >10 |
| 77 | >10 |
| 78 | >10 |
| 79 | >10 |
| 80 | >10 |

TABLE II-continued

IC 50 values for the inhibition of the chymotrypsin-like activity of 20S proteasome.

| Compound # | IC$_{50}$ µg/mL |
|---|---|
| 81 | >10 |
| 82 | >10 |
| 83 | >10 |
| 84 | >10 |
| 85 | >10 |
| 86 | >10 |
| 87 | >10 |
| 88 | >10 |
| 89 | >10 |
| 90 | >10 |
| 91 | >10 |
| 92 | >10 |
| 93 | >10 |
| 94 | >10 |
| 95 | >10 |
| 96 | >10 |
| 97 | >10 |
| 98 | >10 |
| 99 | >10 |
| 100 | >10 |
| 101 | >10 |
| 103 | >10 |
| 104 | >10 |
| 105 | >10 |
| 106 | >10 |
| 107 | >10 |
| 108 | >10 |
| 109 | >10 |
| 110 | >10 |
| 111 | >10 |
| 113 | >10 |
| 114 | 10 |
| 115 | 10 |
| 116 | 10 |
| 117 | 10 |
| 118 | 10 |
| 119 | >10 |
| 120 | >10 |
| 121 | >10 |
| 122 | >10 |
| 123 | >10 |
| 124 | >10 |
| 125 | >10 |
| 126 | >10 |
| 127 | >10 |
| 128 | >10 |
| 129 | 10 |
| 130 | 10 |
| 131 | 10 |
| 132 | 10 |
| 133 | 10 |
| 134 | >10 |
| 135 | >10 |
| 136 | >10 |
| 137 | >10 |
| 138 | >10 |
| 139 | >10 |
| 140 | >10 |
| 141 | >10 |
| 142 | >10 |
| 143 | >10 |
| 144 | 10 |
| 145 | 10 |
| 146 | 10 |
| 147 | 10 |
| 148 | 10 |
| 149 | 10 |
| 150 | >10 |
| 151 | >10 |
| 152 | >10 |
| 153 | >10 |
| 154 | >10 |
| 155 | >10 |
| 156 | >10 |
| 157 | >10 |
| 158 | >10 |
| 159 | >10 |
| 160 | >10 |
| 161 | >10 |
| 162 | >10 |
| 163 | >10 |
| 164 | >10 |
| 165 | >10 |
| 166 | >10 |
| 167 | >10 |
| 168 | >10 |
| 169 | >10 |
| 170 | >10 |
| 171 | >10 |
| 172 | >10 |
| 173 | >10 |
| 174 | 5 |
| 175 | >10 |
| 176 | 1 |
| 177 | 10 |
| 178 | >10 |
| 179 | >10 |
| 180 | 5 |
| 181 | 10 |
| 182 | >10 |
| 183 | 10 |
| 184 | >10 |
| 185 | 5 |
| 186 | >10 |
| 187 | >10 |
| 188 | 5 |
| 189 | >10 |
| 190 | 3 |
| 191 | 3 |
| 192 | 3 |
| 193 | >10 |
| 194 | >10 |
| 195 | >10 |
| 196 | >10 |
| 197 | 10 |
| 198 | >10 |
| 199 | >10 |
| 200 | >10 |
| 201 | >10 |
| 202 | >10 |
| 203 | >10 |
| 204 | >10 |
| 205 | >10 |
| 206 | >10 |
| 207 | 10 |

Compounds of this invention prepared according to the method of Example 1 were also tested as follows. The 20S catalytic subunit of the proteasome (also known as the multicatalytic proteinase complex) was purified to homogeneity from bovine brain according to published methods (Wilk S. and Orlowski, M 1983, 40 842 J. Neurochem). The tryptic activity of the complex is measured by the increase in fluorescence following cleavage of the substrate peptide CBZ-D-Ala-Leu-Arg-(7-amino-4-methyl coumarin). The standard in vitro assay consists of 2 µg 20S proteasome, 0.1–1004 g/ml proteasome inhibitor in 200 ml 50 mM HEPES, containing 0.1% sodium dodecyl sulphate, pH 7.5. The proteolytic reaction is initiated by addition of 50 mM flurogenic peptide substrate and allowed to progress for 15 minutes at 37° C. The reaction is terminated by the addition of 100 mL of 100 mM acetate buffer, pH 4.0. The rate of proteolysis is directly proportional to the amount of liberated aminomethylcoumarin which is measured by fluorescent spectroscopy (EX 370nm, EM 430 nm). Compounds 1–207 were tested for tryptic activity inhibition and active as inhibitors at >10 μg/mL.

Example 5

Compounds of this invention prepared according to the method of Example 1 were also tested as follows. The 20S catalytic subunit of the proteasome (also known as the multicatalytic proteinase complex) was purified to homogeneity from bovine brain according to published methods (Wilk S. and Orlowski, M. 1983, 40 842 J. Neurochem). The tryptic activity of the complex is measured by the increase in fluorescene following cleavage of the substrate peptide CBZ D-Ala-Leu-Arg-(7-amino-4-methyl coumarin). The standard in vitro assay consists of 20 μg 20S proteasome, 0.1–100 μg/ml proteasome inhibitor in 200 μL 50 mM HEPES, containing 0.1% sodium dodecyl sulphate, pH 7.5. The proteolytic reaction is initiated by the addition of 5 mM fluorogenic peptide substrate and allowed to progress for 15 minutes at 37° C. The reaction is terminated by the addition of 100 μL of 100 mM acetate buffer, pH 4.0. The rate of proteolysis is directly proportional to the amount of liberated aminomethylcoumarin which is measured by fluorsecent spectroscopy (EX 370 nm, EM 430 nm). Compounds 1–207 were tested for tryptic activity inhibition and were active as inhibitors at >10 μg/mL.

Example 6

Compounds of this invention prepared according to the method of Example 1 were also tested as follows. The 20S catalytic subunit of the proteasome (also known as the multicatalytic proteinase complex) was purified to homogeneity from bovine brain according to published methods (Wilk S. and Orlowski, M. 1983, 40 842 J. Neurochem). The tryptic activity of the complex is measured by the increase in fluorescence following cleavage of the substrate peptide CBZ D-Ala-Leu-Glu-(7-amino-4-methyl coumarin). The standard in vitro assay consists of 2 μg 20S proteasome, 0.1–100 μg/ml proteasome inhibitor in 200 ml 50 mM HEPES, containing 0.1% sodium dodecyl sulphate, pH 7.5. The proteolytic reaction is initiated by the addition of 50 mM fluorogenic peptide substrate and allowed to progress for 15 minutes at 37° C. The reaction is terminated by the addition of mL of 100 mM acetate buffer, pH 4.0. The rate of proteolysis is directly proportional to the amount of liberated aminomethylcoumarin which is measured by fluorescent spectroscopy (EX 370 nm, EM 430 nm). Compounds 1–207 were tested for peptidylglutamyl activity inhibition at >10 μg/mL. Compound 190 was active at 5 μg/mL.

What we claim is:

1. A compound having the following formula:

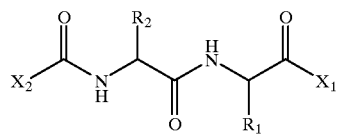

wherein:

$X_2$ is Ar—$X_3$, wherein $X_3$ is —$CH_2CO$, Ar is indole, $R_1$ is isobutyl, $R_2$ is selected from substituted and unsubstituted biphenyl, and $X_1$ is:

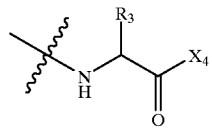

wherein $R_3$ is —$CH_2CO_2H$, and $X_4$ is —OH.

2. The compound of claim 1 wherein $R_2$ is biphenylmethane.

* * * * *

UNITED STATES PATENT AND TRADEMARK OFFICE
CERTIFICATE OF CORRECTION

PATENT NO. : 6,075,150  
DATED : June 13, 2000  
INVENTOR(S) : Wang et al.

Page 1 of 1

It is certified that error appears in the above-identified patent and that said Letters Patent is hereby corrected as shown below:

Column 44,
Compound 169, under heading $R_3$ delete "  " and replace with 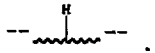.

Compound 170, under heading $R_3$ delete " 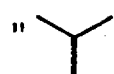 " and replace with 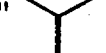.

Column 62,
Line 60, delete "0.1-1004 g/ml" and replace with -- 0.1-100µg/ml --

Column 63,
Line 18, delete "5 mM" and replace with -- 50 mM --.

Signed and Sealed this

Twenty-fifth Day of December, 2001

Attest:

Attesting Officer

JAMES E. ROGAN  
*Director of the United States Patent and Trademark Office*